United States Patent [19]

Bellussi et al.

[11] Patent Number: 4,701,428

[45] Date of Patent: Oct. 20, 1987

[54] CATALYST OF SILICON AND TITANIUM HAVING HIGH MECHANICAL STRENGTH AND A PROCESS FOR ITS PREPARATION.

[75] Inventors: Giuseppe Bellussi, Piacenza; Franco Buonomo, San Donato Milanese; Antonio Esposito, San Donato Milanese; Mario Clerici, San Donato Milanese; Ugo Romano, Vimercate; Bruno Notari, San Donato Milanese, all of Italy

[73] Assignee: Enichem Sintesi S.p.A., Palermo, Italy

[21] Appl. No.: 854,890

[22] Filed: Apr. 23, 1986

[30] Foreign Application Priority Data

Apr. 23, 1985 [IT] Italy ............................... 20457 A/85

[51] Int. Cl.$^4$ ..................... B01J 21/06; B01J 35/08
[52] U.S. Cl. .......................................... 502/8; 502/242

[58] Field of Search .............................. 502/8, 64, 242

[56] References Cited

U.S. PATENT DOCUMENTS 3,329,481  7/1967  Young ........................... 502/64 X
4,410,501 10/1983  Taramasso et al. ............ 502/242 X

*Primary Examiner*—W. J. Shine
*Attorney, Agent, or Firm*—Birch, Stewart, Kolasch & Birch

[57] ABSTRACT

The invention discloses a catalyst on the basis of silicon and titanium having the form of microspheres and constituted by oligomeric silica and by titanium-silicalite crystals having an oligomeric silica/titanium-silicalite molar ratio comprised within the range of from 0.05 to 0.11, wherein the crystals of titanium-silicalite are encaged by means of Si-O-Si bridges.

8 Claims, 6 Drawing Figures

CATALYST OF SILICON AND TITANIUM HAVING HIGH MECHANICAL STRENGTH AND A PROCESS FOR ITS PREPARATION.

The present invention relates to a catalyst on the basis of silicon and titanium, having a high mechanical strength, formed by microspheres and constituted by oligomeric silica and crystals of titanium-silicalite.

In the U.S. Pat. No. 4,410,501 and patent application Ser. Nos. 480,947 and 513,807 the preparation of titanium-silicalite, its use as catalyst in the process of introduction of hydroxy groups into aromatic hydrocarbons by hydrogen peroxide and its use as catalyst in the process of epoxidation of olefinic compounds by hydrogen peroxide respectively, are disclosed. The practical use of the so disclosed catalyst poses some problems relating to the separation and recovery of the same from the reaction mixture; in fact, the very small sizes of the individual crystals, smaller than 5 $\mu$m, render with extreme difficulty their separation from a liquid medium. On the other hand, small sizes of the crystallites of zeolite are essential in liquid phase reactions in order to favour the diffusion of the reactants and of the reaction products, and hence obtain the highest performance. Due to such a reason, the crystallization conditions are controlled to the purpose of obtaining the zeolite in crystals having dimensions as small as possible.

The difficulties inherent in the separation of the catalyst from the reaction medium and the need of recovering the catalyst to the greatest extent can seriously jeopardize the possibility of use of the catalyst in an industrial process. In fact, due to the high cost of the raw products and to the complexity of the zeolite (titanium-silicalite) production process, the cost of the latter is very high, and its incidence on the production cost of organic substrates is considerable, so that the recovery and recycling of the zeolite must be secured to the greatest extent.

It has been surprisingly found that the small crystals of titanium-silicalite produced according to the prior art can be agglomerated with each other, giving rise to a catalyst which is more active and more selective that the single original crystals.

The catalyst, according to the present invention, on the basis of silicon and titanium, is formed by microspheres having a diameter preferably comprised within the range of from 5 to 1000 $\mu$m, and constituted by oligomeric silica and crystals of titanium-silicalite with an oligomeric silica/titanium-silicalite molar ratio comprised within the range of from 0.05 to 0.11, wherein the crystals of titanium silicalite are encaged by means of Si-O-Si bridges.

The process for the preparation of the catalyst is based on the use of an aqueous solution of silica and tetraalkyl-ammonium hydroxide obtained by hydrolyzing a tetraalkyl-silicate, preferably tetraethyl-orthosilicate, in an aqueous solution of tetraalkyl-ammonium hydroxide.

The alkyl groups contained in the tetraalkyl-ammonium ion have a number of carbon atoms comprised within the range of from 1 to 5.

The hydrolysis is carried out in the liquid phase at a temperature comprised within the range of from room temperature to 200° C., preferably 40° C. to 100° C., and more preferably within a time comprised within the range of from 0.2 to 10 hours.

In such a solution, the silica is present in an oligomeric form and at high enough pH values, i.e., at pH $\geq 10$.

When the crystalline titanium-silicalite formed by very small crystals is dispersed in this solution, the surface of the crystals is partly attacked by the alkalinity of the medium: such a situation favours the formation of stable chemical bonds between the surface of the crystals and the oligomeric silicates in solution. By submitting this dispersion to rapid drying, by means of a spray-dryer, water is eliminated and at the same time the crosslinking of the oligomers occurs, leading to the obtainment of microspheres formed by a tridimensional lattice wherein the crystallites of zeolite are closely encaged by Si-O-Si bridges.

Before being used, the microspheres are calcined first under an inert atmosphere ($N_2$, $H_2$, and so forth), and then under an oxidizer atmosphere at a temperature within the range of from 150° to 700° C., preferably of from 500° to 600° C.

Such a particular shape on one hand guarantees an optimum mechanical strength of the agglomerates, and on the other hand improves the catalytic activity. This is probably due to the induction on the crystals of surface lattice defects, which constitute active centers in the reactions of activation of organic substrates and/or of $H_2O_2$ in reactions involving such systems.

Upon decreasing the percentage of crystalline phase in the agglomerate, the catalytic performance worsens, without great improvements in mechanical strengthes. Tests have been carried out by dispersing into equimolar amounts of different silica sources, such as colloidal silica and sodium silicate, the same amounts of titanium-silicalite and operating as described above, but the products obtained had clearly lower characteristics than the novel catalyst.

The optimum concentration in total solids ($SiO_2$, titanium-silicalite, TAA-OH) of the suspension to be atomized is of from 10 to 40% by weight. By varying the concentration of the solids in the suspension, or the dimensions of the atomizer, the average diameter of the particles obtained can be varied. The diameter of the microspheres of the catalyst can thus be varied within the range of from 5 to 1000 $\mu$m. Thus the most suitable size for the desired application is selected.

The catalyst obtained as hereinabove disclosed can be used in the introduction of hydroxy groups into aromatic substrates by $H_2O_2$ and in the epoxidation of olefins by $H_2O_2$.

The aromatic substrates which can be hydroxylated are e.g. phenol, anisole, toluene, benzene, acetanilide, chlorobenzene, nitrobenzene.

The hydroxylating reaction is carried out at temperatures comprised within the range of from 80° C. to 120° C. under room pressure in suitable solvents selected among: methanol, acetone, methylisobutylketone, tert-.butyl alcohol or any solvent mixible, also partially, with water; or at higher temperatures by operating under pressure.

BRIEF DESCRIPTION OF THE DRAWINGS

The present invention will become more fully understood form the detailed description given hereinbelow and the accompanying drawings which are given by way of illustration only and thus are not limitative of the present invention and wherein.

Some examples shall be now supplied to the purpose of better illustrating the invention, which Examples must not be considered as a limitation of the same invention.

EXAMPLE 1

Titanium-silicalite is prepared as follows: 497 g of $TiOCl_2$ is dissolved in 26,350 g of an aqueous solution of tetrapropyl-ammonium hydroxide (TPA-OH$^-$) at 14% by weight and to the solution 14,538 g of colloidal silica at 30% is added under vigorous stirring. The mixture is heated to 60° C. and is kept stirred for about 2 hours; 29,680 g of demineralized water is then added and the whole is stirred for a further hour at 60° C. The clear solution having the following molar composition:

5TPA-OH; $TiO_2$; 20$SiO_2$; 800$H_2O$ is charged into an autoclave equipped with stirring means and is heated, under stirring, at 170° C. for three hours.

The milky suspension obtained, containing the microcrystals of zeolite in suspension, is centrifuged and the cake is washed by redispersing it in water and is totally recovered by subsequent centrifugation (3500 g of titanium-silicalite).

At the same time, 1346 g of tetraethyl-silicate is added under vigorous stirring to 1437 g of solution of tetrapropyl-ammonium hydroxide at 12% by weight and the mixture is heated 1 hour at 60° C., 5890 g of demineralized water is then added and the stirring is continued for a further hour. A clear solution is thus obtained, into which the previously prepared titanium-silicalite is accurately dispersed.

The milky suspension resulting from such dispersion is fed to a spray-dryer (disc-atomizer NIRO ATOMIZER; temperature of entering air 300° C.; temperature of outgoing air 120° C.; diameter of the chamber 1.5 m), compact microspheres having an average diameter close to 20 μm being obtained.

The atomized material is charged into a muffle under a $N_2$ atmosphere and is heated to 550° C. After a two hours permanence at that temperature under a $N_2$ atmosphere, the atmosphere is gradually turned from $N_2$ into air, and the product is kept further for two hours at 550° C. in air. The catalyst obtained has the following molar chemical composition:

1$TiO_2$; 43$SiO_2$.

A sample of catalyst prepared as disclosed in Example 1 and a sample of titanium-silicalite prepared according to the U.S. Pat. No. 4,410,501 are dispersed in water by using a magnetic stirrer and are kept stirred for 5 minutes.

Figure 1:
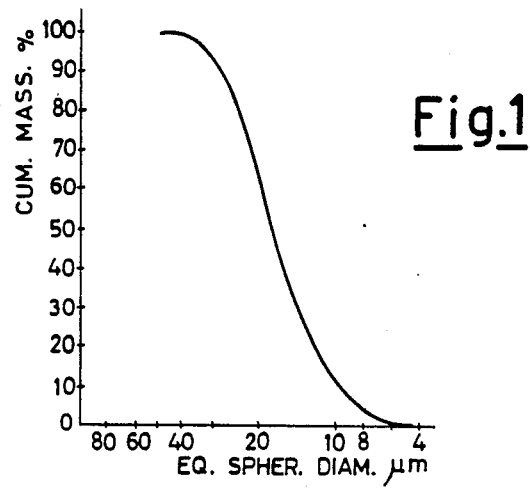
FIGS. 1 and 2 show the granulometric distribution by relating the equivalent spherical diameter with the percent of integrated mass of the catalyst particles.
Figure 2:
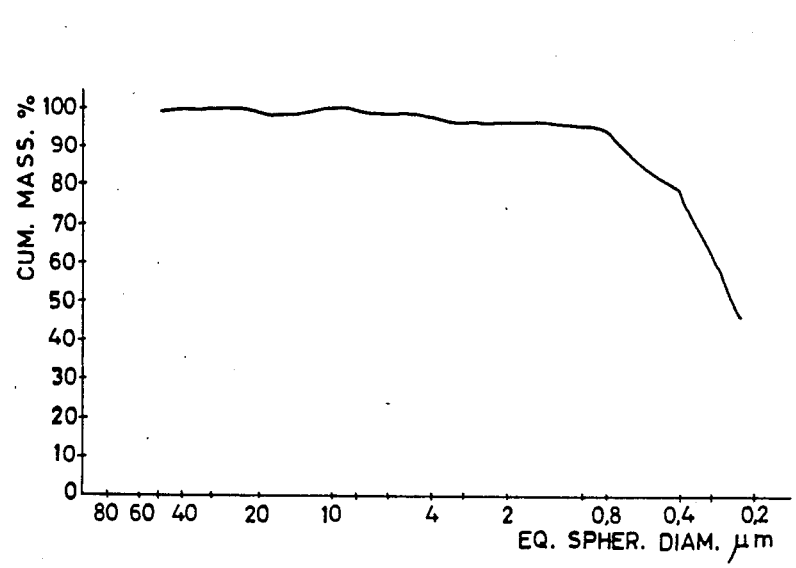
Figure 3:
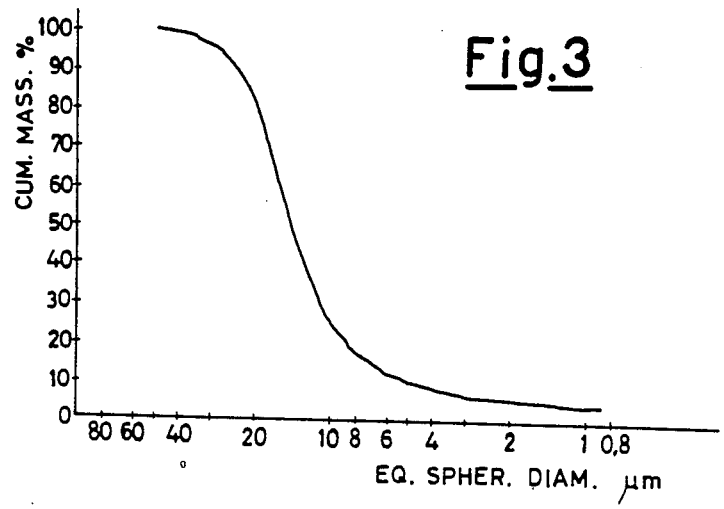
FIGS. 3 and 4 show the same relationship as FIGS. 1 and 2 when the microspheres of catalyst undergo stress inside a liquid medium and are submitted to ultrasound for a fixed period of time.
Figure 4:
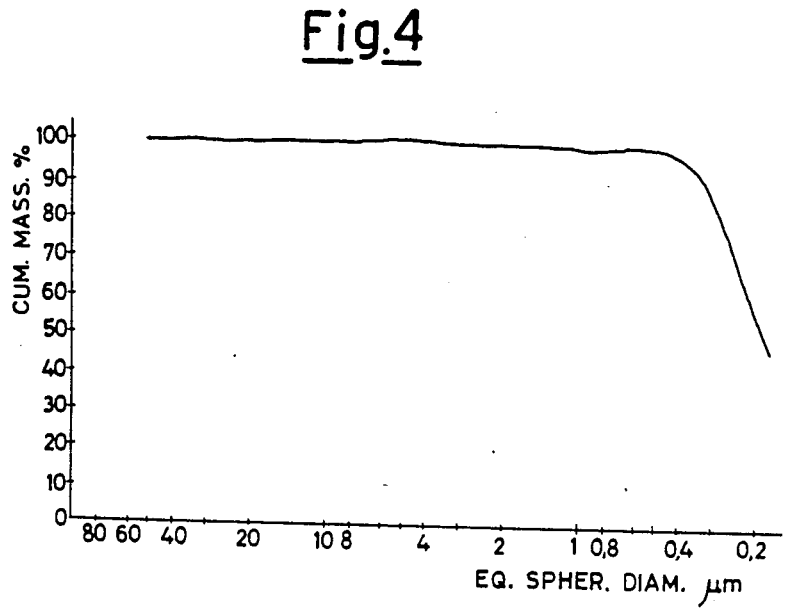

The granulometric distribution of the two samples, as determined by Sedigraph 5000 D, is respectively reported in the charts of FIGS. 1 and 2, wherein as the abscissae the equivalent spherical diameter (as μm) and as the ordinates the percent integrated mass are reported. In order to verify the stability of the microspheres of catalyst prepared according to Example 1 when these undergo mechanical stresses inside a liquid medium, the same samples are submitted to ultrasounds for three hours, and on them the new curves of granulometric distribution, reported in FIGS. 3 and 4, are determined. It can be seen from this test that while the catalyst prepared according to Example 1 maintains unchanged the morphological characteristics of the microspheres, of average size around 20 μm, the catalyst on the basis of titanium-silicalite only shows a further dispersion caused by the breakdown of the crystalline aggregates into single crystalline units. This latter situation simulates the state in which titanium-silicalite actually is, under actual conditions of use, and allows realizing the difficulties to be faced in the separation and recovery from the liquid medium.

EXAMPLE 2 (COMPARISON)

A synthesis is carried out by the procedure and the reactants as used in Example 1, with the exception that the dispersing solution, into which titanium-silicalite is dispersed before being atomized, is obtained by the following procedure:

An amount of 970 g of colloidal silica (Ludox AS 40%) is added under stirring to 6500 g of deionized water and the stirring is continued until a homogeneous solution is obtained.

The molar composition of the catalyst obtained is the following:

1$TiO_2$; 43$SiO_2$.

Figure 5:
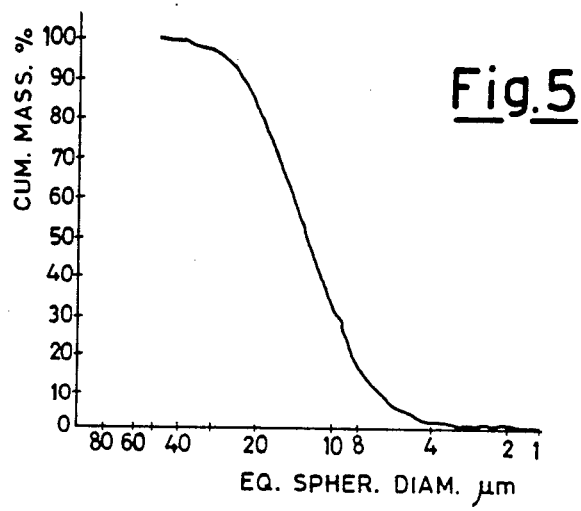
FIG. 5 shows the granulometric distribution of the catalyst as determined by Sedigraph 5000D.

In FIG. 5 the curve of granulometric distribution of this catalyst, as determined by Sedigraph 5000 D, is reported.

Figure 6:
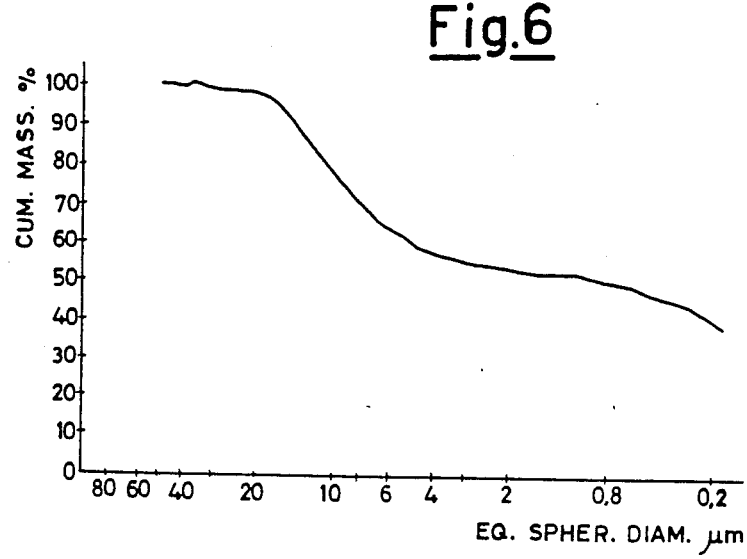
FIG. 6 shows the granulometric distribution of the catalyst after treatment for a fixed period of time within an ultrasound bath.

In FIG. 6 the curve of granulometric distribution of the same catalyst, after a three hours treatment within ultrasound-bath, is reported. From FIGS. 1 and 3 and from FIGS. 5 and 6 it can be seen how the resistance to stresses of this catalyst is considerably worse than of the product prepared according to Example 1.

EXAMPLE 3

Into a 10-l flask 2394 g of phenol, 301 g of $H_2O$, 210 g of acetone, 126 g of catalyst of Example 1 are charged.

The whole is heated and when the system has reached its thermal equilibrium conditions (90° C.), 781 g of $H_2O_2$ at 35% w/v is added.

After 1 hour of reaction, the mixture is cooled and analyzed. From the analysis of the reaction mixture the following results are obtained:

| | |
|---|---|
| % by weight of pyrocatechol + hydroquinone: | 15.52 |
| % of pyrocatechol: | 7.95 |
| Hydroquinone: | 7.57 |
| % yield of $H_2O_2$: | 73.8 | wherein the yield of $H_2O_2$ is: $100 \times \dfrac{\text{mol of diphenols obtained}}{\text{mol of } H_2O_2 \text{ charged}}$ In the operations of separation and recovery of the catalyst from the reaction mixture, by operating with a blue-band filter paper, the catalyst is recovered by 99%.

EXAMPLE 4

The procedure and the amounts of reactants are the same as of Example 3, but this time the catalyst is titanium-silicalite, as per the U.S. Pat. No. 4,410,501.

From the analysis of the reaction mixture of the following results are obtained:

| | |
|---|---|
| % by weight of diphenols: | 14.56 |
| % of pyrocatechol | 7.56 |
| % of hydroquinone | 7.0 |
| % yield of $H_2O_2$ | 69.2 |

In the operations of filtration of the catalyst from the reaction mixture, by using a blue-band filter paper, the recovery efficiency is of 56%.

EXAMPLE 5

The procedure and the amounts of reactants are the same as of Examples 3 and 4; 3 g of catalyst according to Example 2 are used.

From the analysis of the reaction mixture the following results are obtained:

| | |
|---|---|
| % by weight of diphenols: | 14.10 |
| % of pyrocatechol | 7.35 |
| % of hydroquinone | 6.75 |
| % yield of $H_2O_2$ | 67.1 |

In this case the recovery of the catalyst from the reaction mixture, carried out in this case too by using a blue-band filter paper, has occurred to the extent of 80% of the amount charged.

EXAMPLE 6

Into a 250-cc flask equipped with a spherical-bulb condenser, 30 cc of anisole, 70 cc of acetone and 3.5 g of catalyst prepared according to Example 1 are stirred; the mixture is heated to 70° C. and then to it 7.5 cc of $H_2O_2$ at 36% w/v is added dropwise.

At the end of the reaction the following results are achieved:

| | |
|---|---|
| $H_2O_2$ yield | 72.8% |
| anisole conversion | 22.7% |
| anisole yield | 90.6% |
| (pitches)/(pitches + products) | 6.2% |
| Distribution of products: | |
| guaiacol | 36% |
| hydroquinone monomethyl ether | 64% |

The recovery of the catalyst by filtration over blue-band filter paper is carried out with an efficiency of 100%.

EXAMPLE 7

Into a steel autoclave of 1 liter, equipped with mechanical stirrer, temperature control system (reaction temperature=T±1° C.), control means to operate under constant pressure, 190 g of water, 280 g of methanol, 5 g of catalyst (prepared as in Example 1) are charged.

Into a container connected to the autoclave, 60 g of 34% (w/w) $H_2O_2$ are charged. After having isothermed at 40° C. and pressurized by propylene at the pressure of 6 abs. atm (kept constant during the whole test time), the hydrogen peroxide is added to the suspension contained in the autoclave, with vigorous stirring.

The reaction is monitored by drawing samples at time intervals, and analyzing them. Hydrogen peroxide is titrated by iodimetry and the reaction products are analyzed by gas-chromatography.

After 1 hour the following situation has occurred:

| | |
|---|---|
| $H_2O_2$ conversion | 97% |
| Selectivity (referred to $H_2O_2$) to propylene oxide | 92% |
| Selectivity (referred to $H_2O_2$) to 1-methoxy-2-hydroxypropane | 4% |
| Selectivity (referred to $H_2O_2$) to 2-methoxy-1-hydroxypropane | 2.5% |
| Selectivity (referred to $H_2O_2$) to propylene glycol | 1% |

EXAMPLE 8

The test is carried out by the equipment and the procedure as of Example 7. The reactants used are 500 g of $CH_3OH$, 4.4 g of catalyst (as of Example 1), 51 g of 34% (w/w) $H_2O_2$. The reaction temperature is of 40° C. and propylene pressure is 4 abs. atm. After 45 minutes of reaction, the following situation has occurred:

| | |
|---|---|
| $H_2O_2$ conversion | 97% |
| Selectivity (referred to $H_2O_2$) to propylene oxide | 92% |
| Selectivity (referred to $H_2O_2$) to 1-methoxy-2-hydroxypropane | 4% |
| Selectivity (referred to $H_2O_2$) to 2-methoxy-1-hydroxypropane | 2% |
| Selectivity (referred to $H_2O_2$) to propylene glycol | 0.3% |

EXAMPLE 9

Into a steel autoclave of 1 liter, equipped with mechanical stirrer, system for the control of the reaction temperature (T±1° C.), 450 g of methanol, 100 g of 1-octene, 5 g of catalyst (as of Example 1) are charged.

Into a container connected to the autoclave, 50 g of 34% (w/w) $H_2O_2$ are charged. After having isothermed at 45° C. and under stirring, the hydrogen peroxide is added to the suspension contained in the autoclave.

The proceeding of the reaction is monitored by drawing samples at regular time intervals. Hydrogen peroxide is determined by iodimetric titration and the reaction products are determined by gas-chromatography.

After 1 hour the situation is:

| | |
|---|---|
| $H_2O_2$ conversion | 92% |
| Octene conversion | 51.5% |
| Selectivity to 1,2-epoxy-octane | 93% |
| Ethers + glycol | 6.5% |

EXAMPLE 10

The test is carried out by the procedure and the equipment as of Example 9. Into the autoclave 400 g of methanol, 100 g of allyl chloride and 10 g of catalyst are charged; into the container, 70 g of 34% (w/w) $H_2O_2$ is charged. The reaction is carried out at the temperature of 60° C. After 30 minutes, the situation is:

| | |
|---|---|
| $H_2O_2$ conversion | 98% |
| Allyl chloride conversion | 52.3% |
| Selectivity to epichlorohydrin (referred to $H_2O_2$) | 93% |

EXAMPLE 11

A reaction of propylene epoxidation is carried out in continuous by using an equipment consisting in a steel reactor of 0.5 l in volume, equipped with mechanical stirring means, automatic level control, temperature control system, device for operating under a constant propylene pressure, inlet for propylene gas, inlet for the hydrogen peroxide solution, outlet provided with filtering candle of suitable porosity so as to keep the catalyst inside the reactor.

To exemplifying purposes, a test is described, which has been carried out under 15 abs. atm of propylene, with hydrogen peroxide at 2% in water-methanol (40/60 w/w) being fed at a flow rate of 0.4 l/hour, with a constant volume inside the reactor of 0.15 l, 8 g of catalyst (as of Example 1, average granulometry 20 $\mu$m), temperature 42° C.

During the first 40 hours of reaction, the conversion of $H_2O_2$ decreases slowly from the initial value of 90% to the value of 68%, to definitively stabilize at the value of 60%.

The selectivity to propylene oxide, referred to $H_2O_2$, increases with time and after the initial hours stabilizes at the value of 93%.

After 400 hours of continuous running the results are:

| | |
|---|---|
| $H_2O_2$ conversion | 60% |
| selectivity to propylene oxide (referred to $H_2O_2$) | 93% |
| selectivity to 1-methoxy-2-hydroxypropane | 3% |
| selectivity to 2-methoxy-1-hydroxypropane | 2% |
| selectivity to propylene glycol | 1.7% |

The matter balances relatively to hydrogen peroxide are in the overall higher than 99%.

A check on the recovered catalyst does not show any losses of the same during the course of the whole reaction. A plurality of checks carried out by sedimetric and microscopic procedures show that no changes have occurred in the morphologic characteristics of the catalyst.

EXAMPLE 12

The reaction of propylene epoxidation is carried out in a way exactly similar to that described in Example 11.

As the catalyst, the catalyst prepared according to the U.S. Pat. No. 4,410,501 with granulometry similar to that of the catalyst of Example 11 is used.

In this case, the course of the reaction is different: in fact, during the first 40 hours of running, the conversion of $H_2O_2$ decreases from an initial value of 88% to a value of 52%, while the selectivity to propylene oxide increases up to a maximum value of 91%. After 200 hours of continuous operation, the situation is as follows:

| | |
|---|---|
| $H_2O_2$ conversion | 50% |
| selectivity to propylene oxide (referred to $H_2O_2$) | 90% |
| selectivity to 1-methoxy-2-hydroxypropane | 5% |
| selectivity to 2-methoxy-1-hydroxypropane | 3% |
| selectivity to propylene glycol | 1.9% |

The loss of catalyst during the 200 hours of operation has been of 20%.

We claim:

1. A silicon and titanium catalyst, in form of microspheres, comprising oligomeric silica and crystals of titanium-silicalite with an oligomeric silica/titanium-silicalite molar ratio in the range of from 0.05 to 0.11, wherein said crystals of titanium-silicalite are encaged with each other by means of Si-O-Si bridges.

2. Catalyst according to claim 1, wherein said microspheres have a diameter comprised within the range of from 5 to 1000 $\mu$m.

3. A process for the preparation of the catalyst as defined in claim 1 by preparing an aqueous solution of silica and tetraalkyl-ammonium hydroxide by hydrolyzing in the liquid phase a tetraalkyl-orthosilicate in an aqueous solution of tetraalkyl-ammonium hydroxide at a temperature in the range of from room temperature to 200° C. and at a time of from 0.2 to 10 hours; dispersing crystals of titanium silicalite in said aqueous solution, thus forming a suspension of crystals of titanium-silicalite and oligomeric silica; and subjecting said suspension to rapid drying.

4. Process according to claim 3, wherein the tetraalkyl-orthosilicate is tetraethyl-orthosilicate.

5. Process according to claim 3, wherein the hydrolysis takes place at a temperature comprised within the range of from 40° C. to 100° C.

6. Process according to claim 3, wherein the alkyl groups of the tetraalkyl-ammonium have a number of carbon atoms of from 1 to 5.

7. Process according to claim 6, wherein the tetraalkyl-ammonium is tetrapropyl-ammonium.

8. A process for the preparation of the catalyst as defined in claim 2 by preparing an aqueous solution of silica and tetraalkyl-ammonium hydroxide by hydrolyzing in the liquid phase a tetraalkyl-orthosilicate in an aqueous solution of tetraalkyl-ammonium hydroxide at a temperature in the range of from room temperature to 200° C. and at a time of from 0.2 to 10 hours; dispersing crystals of titanium silicalite in said aqueous solution, thus forming a suspension of crystals of titanium-silicalite and oligomeric silica; and subjecting said suspension to rapid drying.

* * * * *